United States Patent
Hanaoka et al.

(10) Patent No.: US 7,236,236 B2
(45) Date of Patent: Jun. 26, 2007

(54) METHODS FOR DETECTING MALARIA PARASITES AND REAGENT KITS THEREFOR

(75) Inventors: Nobuaki Hanaoka, Takatsuki (JP); Yasunori Maekawa, Kobe (JP); Yasumasa Akai, Kobe (JP); Satoshi Nakayama, Kobe (JP)

(73) Assignee: Sysmex Corporation, Hyogo (JP)

( * ) Notice: Subject to any disclaimer, the term of this patent is extended or adjusted under 35 U.S.C. 154(b) by 0 days.

(21) Appl. No.: 10/678,536

(22) Filed: Oct. 3, 2003

(65) Prior Publication Data

US 2004/0067575 A1    Apr. 8, 2004

(30) Foreign Application Priority Data

Oct. 4, 2002  (JP) .............................. 2002-292612

(51) Int. Cl.
   *G01N 37/00*   (2006.01)
(52) U.S. Cl. .............................. 356/36; 356/73; 435/2; 435/26; 435/372; 514/614; 204/547
(58) Field of Classification Search ................. 356/73, 356/36; 435/372, 26, 2; 514/614; 204/547
See application file for complete search history.

(56) References Cited

FOREIGN PATENT DOCUMENTS

GB   2 270 752 A   3/1994
JP   11-75892   3/1999

OTHER PUBLICATIONS

Saito-Ito, A. et al. 2001. A rapid, simple and sensitive flow cytometric system for detection of *Plasmodium falciparum*. Parasitology International 50: 249-257.* van Vianen, P.H. et al. 1993. Flow cytometric screening of blood samples for malaria parasites. Cytometry 14: 276-280.*
Hawley's Condensed Chemical Dictionary (14th Edition, 2002, John Wiley and Sons, Inc.).*
Whaun, J.M.; Rittershaus, C.; and Ip, S.H.C., "Rapid Identification and Detection of Parasitized Human Red Cells by Automated Flow Cytometry", *Cytometry*, 1983, vol. 4, pp. 117-122.
Jacobberger, James W.; Horan, Paul K.; and Hare, J. Donald, "Flow Cytometric Analysis of Blood Cells Stained with the Cyanine Dye DiOC$_1$[3]: Reticulocyte Quantification", *Cytometry*, 1984, vol. 5, pp. 589-600.
Hare, J. Donald; and Bahler, David W., "Analysis of *Plasmodium falciparum* Growth in Culture Using Acridine Orange and Flow Cytometry", *The Journal of Histochemistry and Cytochemistry*, 1986, vol. 34, No. 2, pp. 215-220.
Bianco, A. E.; Battye, F. L.; and Brown, G. V., "*Plasmodium falciparum*: Rapid Quantification of Parasitemia in Fixed Malaria Cultures by Flow Cytometry", *Experimental Parasitology*, 1986, vol. 62, pp. 275-282.
van Vianen, Philip H.; van Engen, Anneloes; Thaithong, Sodsri; van der Keur, Maarten; Tanke, Hans J.; van der Kaay, Hugo J.; Mons, Barend; and Janse, Chris J., "Flow Cytometric Screening of Blood Samples for Malaria Parasites", *Cytometry*, 1993, vol. 14, pp. 276-280.
Saito-Ito, Atsuko; Akai, Yasumasa; He, Shenyi; Kimura, Mikio; and Kawabata, Masato, "A rapid, simple and sensitive flow cytometric system for detection of *Plasmodium falciparum*", *Parasitology International*, 2001, vol. 50, pp. 249-257.

* cited by examiner

*Primary Examiner*—Robert A. Zeman
(74) *Attorney, Agent, or Firm*—Brinks Hofer Gilson & Lione (57) ABSTRACT

Methods for detecting a malaria parasite are described that include: releasing the malaria parasite by allowing an erythrocyte in a specimen to undergo hemolysis; staining the released malaria parasite with a fluorescent dye to prepare a measurement sample; detecting optical information from the measurement sample; and distinguishing the malaria parasite based on the optical information obtained. Apparatuses and reagent kits are also described.

16 Claims, 4 Drawing Sheets

METHODS FOR DETECTING MALARIA PARASITES AND REAGENT KITS THEREFOR

FIELD OF THE INVENTION

The present invention relates to methods for detecting malaria parasites and reagent kits therefore. More particularly, the present invention relates to methods for detecting malaria parasites and reagent kits therefor which enable correct and convenient distinction of malaria parasites using a flow cytometer by allowing an erythrocyte in a sample to undergo hemolysis in two steps.

BACKGROUND

Malaria is a parasitic infection disease which is prevalent in tropical and subtropical zones. Based on statistics from the World Health Organization (WHO), 40% or more of the worldwide population lives in malaria-prevalent regions, 3 to 5 hundred million people per year are infected, and 1.5 to 3 million cases are assumed to result in death.

Malaria is mediated by a mosquito called Anopheles. When an Anopheles mosquito bites human skin, a parasite is injected into human blood together with the saliva of the Anopheles mosquito. The parasite travels into a hepatocyte, where it proliferates, and then is released again into the blood. At this time, the morphology of the parasite is referred to as a merozoite, which invades an erythrocyte soon after being released into the blood and then grows while changing its morphology. This change in the morphology is referred to as a life cycle, each stage of which is referred to as a ring form, tropozoite or schizonte. A parasite which has grown up to the stage of the schizonte destroys an erythrocyte, and then is released as a merozoite again into the blood. The released merozoite invades an erythrocyte, and repeats the life cycle again, thereby proliferating repeatedly. The malaria parasite proliferates by repeating this cycle, while destroying erythrocytes in the blood continuously. The merozoite is differentiated partly into a morphology referred to as a gametocyte without infecting the erythrocyte. The gametocyte serves as a further source of infection via the bloodsucking of an Anopheles mosquito.

The measurement method typically employed in diagnosing malaria is a method in which a blood smear preparation is stained, for example by a Giemsa staining method or a nucleic acid-staining fluorescent dye method, and then examined visually by microscopic observation using an optical microscope or a fluorescent microscope.

However, this method requires a complicated and time-consuming process involving smear preparation, fixation and staining. In addition, it requires a well-trained operator for ensuring correct detection and identification since detection and identification of the malaria parasite are performed visually. Moreover, it requires a long observation period and the observation of a large number of erythrocytes in order to ensure highly sensitive detection since a specimen to be tested from a malaria patient may have a low % infection. Accordingly, the results of the measurement may frequently be inaccurate. Moreover, it is difficult to handle a large number of specimens due to the time-consuming pretreatment and measurement stages.

Recently, methods that do not involve microscopic examination were developed, for example DNA probe method, indirect fluorescent antibody method, and indirect erythrocyte aggregation method. However, all of these methods also have disadvantages, such as complicated operation, time-consuming measurement periods, costly procedures, and the like.

In an effort to overcome these disadvantages, a method for measuring malaria parasite using flow cytometry has been developed. In this method, malaria parasite is stained with a nucleic acid-staining dye and then measured by a flow cytometer. This method mostly involves automatic measurement and involves extremely low error as compared to microscopic examination. It is also rapid and convenient since measurement times are on the order of tens of seconds to several minutes and a large number of specimens may be handled at once (for example, see J. M. Whaum et al., *Cytometry*, 1983, 4, 117; J. W. Jacobberger, *Cytometty*, 1984, 5, 589; J. D. Hare, *J. Histochem. Cytochem.*, 1986, 34, (2) 215; and A. E. Bianco et al., *Experi. Parasitol.*, 1986, 62, 275).

Nevertheless, the position corresponding to the appearance of malaria-infected erythrocyte may sometimes overlap with reticulocyte on the scattergram, thereby complicating the measurement of malaria-infected erythrocyte, which leads to measurement error as well as to a reduction in measurement sensitivity.

In order to solve this problem, a method was proposed in which erythrocyte is allowed to undergo hemolysis using hemolytic agent containing formaldehyde and ethylene glycol to release the malaria parasite which is then stained and measured by a flow cytometer (for example, see: P. H. Vienen et al., *Cytometry*, 1993, 14, 276). Alternatively, an erythrocyte is separated exclusively by centrifugation and then allowed to undergo hemolysis chemically or ultrasonically prior to counting (see: GB-A 2270752).

However, even with these methods, there are disadvantages such as complicated operation procedures (e.g., centrifugation and the like) as well as the long times required to perform the operations.

In another proposed method, erythrocyte is allowed to undergo hemolysis using a surfactant, and a blood sample containing a fluorescent-stained malaria parasite is measured using a flow cytometer to obtain forward scattering light intensity and lateral fluorescent light intensity from which a scattergram is produced and used for distinguishing and detecting various blood cells, debris (e.g., pieces of hemolytically broken erythrocyte), and malaria parasite (see: A. Saito-Ito et al., *Parasitol. Int.*, 2001, 50(4), 249; and Japanese Unexamined Patent Publication No. 11-75892). By this method, cultured malaria can be detected at a higher sensitivity on the basis of each stage of the life cycle.

SUMMARY

The scope of the present invention is defined solely by the appended claims, and is not affected to any degree by the statements within this summary.

A first method for detecting a malaria parasite embodying features of the present invention includes: releasing the malaria parasite by allowing an erythrocyte in a specimen to undergo hemolysis; staining the released malaria parasite with a fluorescent dye to prepare a measurement sample: detecting optical information from the measurement sample; and distinguishing the malaria parasite based on the optical information obtained. The specimen is treated with a first hemolytic agent containing a first surfactant to form a treated specimen. The treated specimen is further treated with a second hemolytic agent containing a second surfac tant having a hemolytic activity higher than that of the first surfactant.

A second method embodying features of the present invention for detecting a malaria parasite in a sample includes: treating the sample with a first hemolytic agent containing a first surfactant to form a first treated sample; treating the first treated sample with a second hemolytic agent containing a second surfactant to form a second treated sample, wherein the second surfactant has a hemolytic activity higher than a hemolytic activity of the first surfactant; staining the second treated sample with a fluorescent dye to form a stained sample; introducing the stained sample into a flow cytometer; detecting fluorescent light information; and distinguishing the malaria parasite based on the fluorescent light information.

An apparatus for automatically detecting a malaria parasite embodying features of the present invention includes: (a) a chamber configured to receive a sample containing a malaria parasite to prepare a measurement sample, wherein the measurement sample is obtained by (i) treating the sample containing the malaria parasite with a first hemolytic agent containing a first surfactant to form a first treated sample, (ii) treating the first treated sample with a second hemolytic agent containing a second surfactant to form a second treated sample, wherein the second surfactant has a hemolytic activity higher than a hemolytic activity of the first surfactant, and (iii) staining the second treated sample with a fluorescent dye; (b) a flow cytometer for detecting fluorescent light information from the measurement sample; and (c) a control unit for distinguishing the malaria parasite based on the fluorescent light information.

A reagent kit for detecting a malaria parasite embodying features of the present invention includes: a first hemolytic agent containing a first surfactant; a second hemolytic agent containing a second surfactant having a hemolytic activity higher than a hemolytic activity of the first surfactant; and a fluorescent dye for staining the malaria parasite.

DETAILED DESCRIPTION

It was found that that when the methods described by A. Saito-Ito (Parasitol. Int.) and in Japanese Unexamined Patent Publication No. 11-75892 were applied to the measurement of blood from an actual malaria-infected patient, reticulocyte still exists that has not undergone sufficient hemolysis, thereby resulting in increased background which makes it difficult to conduct correct measurements of the specimen. However, in accordance with the present invention, it was discovered that by conducting the hemolysis of an erythrocyte in two steps, the effect of reticulocyte can be fully eliminated, thereby enabling correct and highly accurate detection of the malaria parasite.

In accordance with the present invention, an erythrocyte in a specimen is first allowed to undergo hemolysis to release malaria parasite.

The specimen for use in accordance with the present invention may be a clinical blood sample (for example, peripheral blood) that contains malaria-infected erythrocyte, as well as an experimentally cultured fluid or the like. The sample is not limited with regard to the degree of infection as long as it is infected with malaria parasite. The % infection may be 10% or more, and may be 0.01% or less. The sample may also be one which has been treated, for example, with an anticoagulant. The anticoagulant is not limited and may, for example, be EDTA, heparin, citric acid, citrate or the like.

The hemolysis is accomplished by treating a specimen with a first hemolytic agent containing a first surfactant followed by treating the specimen with a second hemolytic agent containing a second surfactant.

The first surfactant contained in the first hemolytic agent preferably does not cause damage to malaria parasite which would affect the measurement. The first surfactant is preferably selected in view of the amount of malaria parasite contained in the specimen (i.e., the % infection, the dilution magnitude and the like). Preferably, a surfactant having a low erythrocyte hemolytic effect is employed. In addition, the surfactant contained in the first hemolytic agent may be a single surfactant or may be a mixture of several surfactants, as long as the desired effect is achieved.

Representative surfactants for use in accordance with the present invention include nonionic, anionic, and cationic surfactants.

Preferably, a nonionic surfactant for use in accordance with the present invention is polyoxyethylene-based and represented by a formula wherein $R_1$ represents an alkyl, alkenyl or alkynyl group having 10 to 22 carbon atoms, $R_2$ represents —O—, —($C_6H_4$)—O— or —COO—, and n represents an integer from 8 to 120.

The alkyl group having 10 to 22 carbon atoms may be straight or branched, and includes but is not limited to decyl, lauryl, myristyl, palmityl, stearyl, eicosyl, and the like. The alkenyl group having 10 to 22 carbon atoms may be an alkyl group as listed above having one or more double bonds at any suitable positions. The alkynyl group having 10 to 22 carbon atoms may an alkyl group as listed above having one or more triple bonds at any suitable positions.

Representative groups include but are not limited to polyoxyethylene (n) alkylphenyl ether. More particularly, representative groups include but are not limited to polyoxyethylene (40) nonylphenyl ether, polyoxyethylene (100) nonylphenyl ether, polyoxyethylene (10) lauryl ether, and the like.

The concentration of nonionic surfactant may vary depending on the type of surfactant employed. An excessive concentration of surfactant may cause damage to the malaria parasite, which leads to a reduction in the scattering light and/or fluorescent light intensity emitted by the parasite and to undesirable debris from hemolytically broken erythrocytes. For example, when using polyoxyethylene (40) nonylphenyl ether, a suitable concentration is between about 0.1 and about 20 mg/L based on the entire quantity containing the specimen upon treatment, while it is between about 0.1 and about 30 mg/L when using polyoxyethylene (100) nonylphenyl ether.

Preferably, an anionic surfactant for use in accordance with the present invention is a polyoxyethylene-based anionic surfactant represented by formula wherein $R_1$, $R_2$ and n are as defined above, and X represents $SO_3Na$, COONa, $OSO_3Na$ or ONa.

The concentration of anionic surfactant may vary depending on the type of surfactant employed.

Preferably, a cationic surfactant for use in accordance with the present invention is represented by formula wherein $R^a$ represents an alkyl, alkenyl or alkynyl group having 8 to 20 carbon atoms, each of $R^b$, $R^c$ and $R^d$, independently, represents an alkyl, alkenyl or alkynyl group having 1 to 8 carbon atoms, each of $X^-$ and $Y^-$, independently, represents an anion, and m represents an integer from 7 to 19.

The alkyl having 8 to 20 carbon atom may be straight or branched, and includes but is not limited to octyl, decyl, lauryl, myristyl, palmityl, stearyl, eicosyl and the like. The alkenyl group having 8 to 20 carbon atoms may be an alkyl group as listed above having one or more double bonds in any suitable positions. The alkynyl group having 8 to 20 carbon atoms may be an alkyl group as listed above having one or more triple bonds in any suitable positions. Representative alkyl groups having 1 to 8 carbon atoms include but are not limited to methyl, ethyl, propyl, butyl, isobutyl, pentyl, hexyl, heptyl, octyl, and the like. Representative alkenyl groups having 1 to 8 carbon atoms may be an alkyl as listed above having one or more double bonds at any suitable positions, while representative alkynyl groups having 1 to 8 carbon atoms may be an alkyl as listed above having one or more triple bonds at any suitable positions. Presently preferred $R^a$ groups include octyl, decyl, lauryl, myristyl, cetyl, and the like. Presently preferred $R^b$ to $R^d$ groups include methyl, ethyl, propyl, isopropyl, and the like.

Representative anions include halide ions such as fluorine, chlorine, bromine and iodine ions, as well as $CF_3SO_3^-$, $BF_4^-$, $ClO_4^-$, and the like.

Representative cationic surfactants include octyltrimethylammonium bromide (OTAB), decyltrimethylammonium bromide (DTAB), lauryltrimethylammonium chloride (LTAC), myristyltrimethylammonium bromide (MTAB), cetylpyridinium chloride (CPC), and the like.

The concentration of cationic surfactant should be selected in consideration of the fact that an increase in the total number of carbons in $R^a$ to $R^d$ contained in the surfactant results in increased hemolytic activity. An excessive surfactant concentration is not desirable since it also dissolves malaria parasite. In accordance with the present invention, MTAB (total number of carbons=17) is used preferably in an amount of about 300 to about 3000 mg/L, LTAC (total number of carbons=15) in an amount of about 300 to about 10000 mg/L, DTAB (total number of carbons=13) in an amount of about 5000 to about 20000 mg/L, OTAB (total number of carbons=11) in an amount of about 21000 to about 40000 mg/L, based on the total quantity containing the specimen upon treatment. Surfactants other than those listed above may also be employed, such as Triton X-100 (polyethylene glycol mono[p-(1,1,3,3-tetramethylbutyl)phenyl] ether), CHAPS (3-[(3-chloroamidopropyl)dimethylammonio] propanesulfonic acid), CHAPSO (3-[(3-chloroamidopropyl)dimethylammonio]-2hydroxypropanesulfonic acid), BIGCHAP (N,N-bis(3-D-gluconamidopropyl)deoxychloramide), sucrose monocaprate, sucrose monocholate, n-octyl-α-D-glucopyranoside, n-heptyl-α-D-thioglucopyranoside, n-octyl-α-D-thioglucopyranoside, n-dodecyl-α-D-maltopyranoside, n-nonyl-α-D-thiomaltopyranoside, and the like.

A first hemolytic agent containing a first surfactant usually contains water or an organic solvent containing a buffering agent or a chelating agent described above in addition to the surfactant. As used herein, an organic solvent may be one having no effect on an erythrocyte or malaria parasite contained in a blood sample, and is preferably one capable of dissolving and retaining a nucleic acid-staining dye in a stable manner when such a dye is contained in the first hemolytic agent, as described below. Representative water-soluble, non-aqueous solvents include methanol, ethanol, ethylene glycol, dimethyl sulfoxide, and the like.

The treatment with a first hemolytic agent should be done so that sufficient accuracy can be achieved in the subsequent quantitative measurement by flow cytometry. For example, the reaction temperature is about 20 to about 50° C., with the reaction time being suitably between about 5 and about 300 seconds. While accuracy is generally higher when the hemolytic reaction is completed, it is not necessary that the reaction be completed provided that the resultant accuracy is within an acceptable range.

The second surfactant contained in the second hemolytic agent is preferably one that can accomplish sufficient hemolysis of an erythrocyte, especially reticulocyte remaining after hemolytic treatment with the first hemolytic agent, without causing any damage to malaria parasite that would affect the measurement.

The second surfactant may be selected from the representative first surfactants in view of the type of the first surfactant, the type and condition of the sample, and the like, and can be used in controlled concentrations. The second surfactant is preferably one having a hemolytic activity which is higher than that of the first surfactant. The composition of the hemolytic agent can also be adjusted as described above. The surfactant is preferably one of a type that is different from the first surfactant. Especially when a nonionic surfactant is used as the first surfactant, then the second surfactant is preferably a cationic or anionic surfactant. Typically, when about 0.1 to about 20 mg/L of polyoxyethylene (40) nonylphenyl ether is employed as the first surfactant, then the second surfactant is preferably about 300 to about 10000 mg/L of lauryltrimethylammonium chloride.

The treatment with the second hemolytic agent can suitably be conducted under conditions similar to those used for the treatment with a first hemolytic agent.

In accordance with the present invention, a released malaria parasite is further stained with a fluorescent dye to prepare a measurement sample. This staining may be conducted simultaneously with or subsequently to the treatment with a first hemolytic agent, or may be conducted simultaneously with or subsequently to the treatment with a second hemolytic agent. Thus, the first hemolytic agent and/or the second hemolytic agent may be supplemented with a dye in addition to the surfactant. The hemolytic agent may be used to treat the sample thereby accomplishing the staining, or the staining may be conducted by adding a dye to the sample after treatment with the first hemolytic agent or the second hemolytic agent. Especially when the fluorescent dye is unstable in aqueous solution, it may be dissolved in a water-soluble, non-aqueous solvent as described above, and mixed with the treated sample immediately before being introduced into a flow cytometer, thereby staining malaria parasite.

The fluorescent dye is not limited as long as it can stain a nucleic acid. Representative dyes include but are not limited to acridine orange, thiazole orange, ethidium bromide, propidium iodide, auramine O, Hoechst 33258, Hoechst 33342, rhodamine 123, and DiOC1(3). Any of these fluorescent dyes can be used when an argon laser (488 nm) is employed as the light source.

When using light of other wavelengths, such as a red color laser, a dye capable of being used therewith is preferably employed. An example of such other dyes is represented by formula wherein $R_1$ represents a hydrogen atom or a lower alkyl group; each of $R_2$ and $R_3$, independently, represents a hydrogen atom, a lower alkyl group or a lower alkoxy group; $R_4$ represents a hydrogen atom, an acyl group or a lower alkyl group; $R_5$ represents a hydrogen atom or an optionally substituted lower alkyl group; Z represents a sulfur atom, an oxygen atom or a carbon atom substituted by two lower alkyl groups; n represents 1 or 2; and $X^-$ represents an anion.

An alternative dye may be employed, which is represented by formula wherein $R_1$ represents a hydrogen atom or an alkyl group; each of $R_2$ and $R_3$, independently, represents a hydrogen atom, a lower alkyl group or a lower alkoxy group; $R_4$ represents a hydrogen atom, an acyl group or an alkyl group; Z represents a sulfur atom, oxygen atom or carbon atom substituted by two lower alkyl groups; n represents 0, 1 or 2; and $X^-$ represents an anion.

Other dyes (available from Molecular Probes, Inc.) that may be employed include but are not limited to acridine homodimer, actinomycin D, 7-aminoactinomycin D (7-AAD), 9-amino-6-chloro-2-methoxyacridine (AGMA), BOBO-1, BOBO-3, BO-PRO-1, BO-PRO-3, 4',6-diamidino-2-phenylindole (DAPI), dihydroethidium, 4',6-(diimidazolin-2-yl)-2-phenylindole, ethidium-acridine heterodimer, ethidium diazide, ethidium homodimer-1, ethidium homodimer-2, ethidium monoazide, hexidium iodide, hydroxystilbamidine, methanesulfonate, LDS 751, OilGreen ssDNA quantitation reagent, PicoGreen dsDNA quantitation reagent, PO-PO-1, PO-PO-3, PO-PRO-1, PO-PRO-3, SYTO 11 live-cell nucleic acid stain, SYTO 12 live-cell nucleic acid stain, SYTO 13 live-cell nucleic acid stain, SYTO 14 live-cell nucleic acid stain, SYTO 15 live-cell nucleic acid stain, SYTO 16 live-cell nucleic acid stain, SYTO 20 live-cell nucleic acid stain, SYTO 21 live-cell nucleic acid stain, SYTO 22 live-cell nucleic acid stain, SYTO 23 live-cell nucleic acid stain, SYTO 24 live-cell nucleic acid stain, SYTO 25 live-cell nucleic acid stain, SYTO 17 red fluorescent nucleic acid stain, SYTOX green nucleic acid stain, TO-PO-1, TO-PRO-3, TO-PRO-5, TO-TO-1, TO-TO-3, YO-PRO-1, YO-PRO-3, YO-YO-1, YO-YO-3, and the like.

While the amount of fluorescent dye may vary depending on the type of dye employed, a preferred amount is generally between about 0.001 and about 10000 ppm based on the total quantity containing the specimen upon treatment, more preferably about 0.005 to about 1000 ppm, and more preferably about 0.01 to about 500 ppm.

A sample, a first hemolytic agent and/or a second hemolytic agent according to the invention may contain a buffering agent for the purpose of maintaining a constant pH. The buffering agent is employed so that a stable result of the malaria parasite staining will be obtained via maintenance of a constant pH. Usually it is used in a concentration ranging from several mM to about 100 mM. The type of buffering agent is not limited, and is preferably employed in conventional amounts. Representative buffering agents include but are not limited to carboxylic acids, phosphoric acid, Good's buffer such as tricine, taurine, and the like, which may be selected according to the pH suitable for staining. The suitable pH may vary depending on the dye employed, and is preferably between about 3 and about 11, more preferably between about 4 and about 9.

An osmotic compensation agent may be added. It is preferable to adjust the osmotic pressure to usually about 150 to about 600 mOsm/kg based on the total quantity containing the specimen upon treatment in order to prevent hypotonic dissolution of malaria parasite. The osmotic compensation agent is not limited, and may for example be an alkaline metal salt of propionic acid or the like, as well as a saccharide such as glucose, mannose or the like. An alkaline metal halide such as NaCl or an alkaline earth metal halide may also be employed. It is also possible to use a polyvalent anion. Representative polyvalent anions include but are not limited to sulfate ion, phosphate ion, carbonate ion and polyvalent carboxylate ions, the donors of which may, for example, be citric acid, sulfuric acid, phosphoric acid, EDTA as well as alkaline metal salts thereof. When the osmotic pressure suitable for the measurement can be maintained by a buffering agent, then the buffering agent may also serve as an osmotic compensation agent.

If necessary, a preservative may also be added. Representative preservatives include but are not limited to sodium 2-pyridylthio-1-oxide, β-phenethyl alcohol, and the like.

In accordance with the present invention, malaria parasite is distinguished after the procedure described above.

Stained malaria parasite can be distinguished based on optical information. The optical information may be obtained, for example, by using a flow cytometer. The flow cytometer may be any known flow cytometer. The light source may be selected appropriately depending on the dye employed.

In a distinction procedure using a flow cytometer, a measurement sample is first introduced into the flow cytometer, a cell flowing through a sheath flow is irradiated with an excitation light and the intensity of the light emitted by the cell measured, and malaria parasite is distinguished from other cell components utilizing the difference in light intensity.

The light emitted by a cell may, for example, be scattering light and/or fluorescent light. The scattering light may, for example, be lateral scattering light and/or forward scattering light, while the fluorescent light may, for example, be lateral fluorescent light and/or forward fluorescent light.

The distinction may be accomplished, for example, by utilizing the difference in scattering light intensity and fluorescent light intensity. Typically, the scattering light intensity and the fluorescent light intensity are employed to make a two dimensional distribution diagram (scattergram), which is gated so that the malaria parasites are surrounded (i.e., zoning), and then the cells in each gate are counted, thereby accomplishing the distinction. It is also possible to distinguish malaria parasite from leukocyte on the basis of the fluorescent light intensity.

As a result, it is possible not only to distinguish malaria parasite from other components such as erythrocyte debris or leukocyte but also to classify and count the life stages of the malaria parasite. Usually, all life stages appear in an in vitro culture or in peripheral blood from a patient in the cases of *P. vivax* malaria, *P. malariae* malaria, and *P. ovale* malaria. However, in the case of *P. falciparum* malaria, only the ring form and the gametocyte are found in peripheral blood although all life stages are found in an in vitro culture. Nevertheless, all of these life stages of the malaria parasite can be classified by the method described above. Thus, on the basis of the difference in scattering light intensity and fluorescent light intensity, merozoite, ring form, trophozoite schizonte, and gametocyte can be distinguished from each other. By using this classification of the life stages, and on the basis of the appearance pattern on a scattergram, peripheral blood can be diagnosed to have either the *P. falciparum* malaria exhibiting only the ring form and the gametocyte or the other three malaria exhibiting all life stages. Especially in the case of the falciparum malaria which should be treated immediately after onset, methods embodying features of the present invention are useful in conducting rapid measurement and early diagnosis.

It is also possible that the distinction may be determined based on the frequency distribution of malaria parasite in the measurement sample having a certain range of fluorescent light intensity detected by the flow cytometer. The judgment of the type of the malaria parasite can be accomplished based on the results of the comparison of a standard value with a highest frequency value in the frequency distribution of malaria parasite having a certain range of fluorescent light intensity. It is also possible that the judgment of the malaria parasite is a judgment of whether it is *P. falciparum* malaria or not. The distinction may further include classifying malaria parasite having a certain range of fluorescent light intensity as a ring form.

Figure 6:
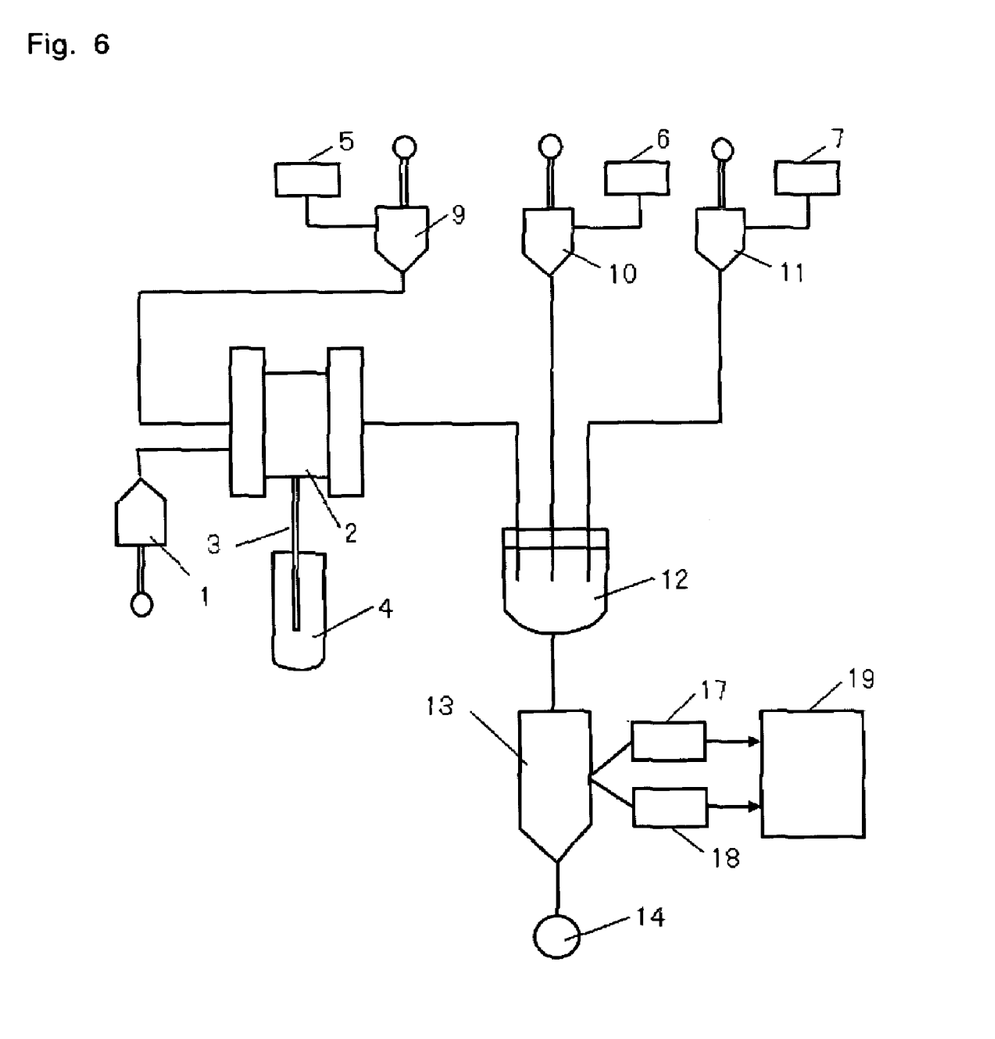
FIG. 6 shows a schematic representation of an apparatus for automatically detecting malaria parasite in accordance with the present invention.

FIG. 6 schematically shows an apparatus in accordance with the present invention for detecting malaria parasite. The dispenser includes an aspiration pump (1), a sampling valve (2), and an aspiration pipette for a sample (3). A reaction chamber can be employed as the means for preparing the sample. The flow cytometer comprises a flow cell (13), a detector for forward scattering light (17), a detector for fluorescence (18), and a data processor (19). The supplier comprises a first lysing agent container (5), a second lysing agent container (6), a staining solution container (7), and aspiration-emission pumps (9)~(11) connected with each container via tubes. A negative pressure pump (14) can be employed as the introduction means.

In practice, the sample of blood in test tube (4) is introduced into the sampling valve (2) through the tube using aspiration pump (1) from the aspiration pipette (3) aspirating the sample. The appropriate amount is quantitatively collected. The quantified sample of blood is introduced into the reaction chamber (12) via the sampling valve (2) via the aspiration emission pump (9) via tube.

The sampling valve in accordance with the present invention is defined to overlap three round-form discs, which may be made of ceramic. The sampling valve comprises a mobile element sandwiched between two fixed elements, in which a flow-in route and/or a flow-out route are set for the fixed elements, and a quantitative analysis route is set for the mobile element. The sample is passed through the flow-in route, quantification route, and flow-out route in order. For the fixed elements, the reagent flow-in route and/or the flow-out route are set, and the mobile elements are rotated to pass the reagent into the flow-in route, quantification route, and flow-out route in order. Next the quantified sample is flowed out into the reaction chamber with the reagent. Such a sampling valve is used in the analytical apparatus for performing blood assay.

To the reaction chamber (12), the first lysing agent collected from the first lysing agent container (5) with the aspiration-emission pump (9) is introduced via the tube through the sampling valve (2) and is mixed with the sample of blood in the chamber (12). Further, the second lysing solution collected in an appropriate amount from the second lysing container (6) with the aspiration-emission pump (10) is introduced into the chamber (12) and mixed with the blood treated with the first lysing solution. Thereafter, the staining solution collected in an appropriate amount from the staining container (7) with the aspiratione-mission pump (11) is introduced into the chamber (12) to stain malaria parasite and other material.

The sample thus obtained is introduced from the chamber (12) to the flow cell (13) via a tube by using the negative pressure pump (14), and scattering light and fluorescence are measured. After measurement, the data for scattering light and fluorescence are detected in the detector for forward scattering light (17) and the detector for fluorescence (18). Then, malaria parasites are distinguished and counted with the data processor (19).

The present invention further provides a reagent kit for detecting malaria parasites. The reagent kit comprises a first hemolytic agent containing a first surfactant, a second hemolytic agent containing a second surfactant and a fluorescent dye for staining malaria parasite, which may be in a two-fluid system containing reagents to be prepared before use or in a three-fluid system.

For example, at least a first hemolytic agent and a second hemolytic agent are packaged separately, and a fluorescent dye for staining malaria parasite may be contained in either or both of the first hemolytic agent and the second hemolytic agent, thereby providing a two-fluid system. Alternatively, the fluorescent dye may be supplied as a solid to be prepared just prior to use by dissolving it in the first hemolytic agent and/or the second hemolytic agent, thereby providing a two-fluid system. Alternatively, the fluorescent dye for staining malaria parasite may be packaged separately from the first hemolytic agent and the second hemolytic agent, thereby providing a three-fluid system. Any types and concentrations of the components contained in these systems (e.g., surfactants, etc.) may be employed in the preparation for enabling the measurement described above.

The following examples and representative procedures illustrate features in accordance with the present invention, and are provided solely by way of illustration. They are not intended to limit the scope of the appended claims or their equivalents.

EXAMPLE 1

A reagent for measuring malaria parasite was prepared as follows.

Four (4) mg of polyoxyethylene (40) nonylphenyl ether was mixed with 500 ml of a 120 mM phosphate buffer (pH9) to prepare a first hemolytic agent. The osmotic pressure of the first hemolytic agent was 307 mOsm/kg.

Five hundred (500) mg of lauryltrimethylammonium chloride and 3 mg of acridine orange were mixed with 500 ml of a 120 mM phosphate buffer (pH9) to prepare a second hemolytic agent. The osmotic pressure of the second hemolytic agent was 318 mOsm/kg.

Two (2) μl of peripheral blood of a *P. falciparum* malaria patient having 0.2% infection (ratio of the malaria parasite-infected erythrocyte count based on total erythrocyte count) was mixed with 500 μl of the first hemolytic agent and incubated at 37° C. for 30 seconds. Next, the resultant sample was mixed with 500 μl of the second hemolytic agent, incubated at 37° C. for 15 seconds, thereby staining the malaria parasite.

The resultant sample was introduced into a flow cytometer provided with an argon laser with a wavelength of 488 nm as an excitation light source, and examined for forward scattering light intensity and lateral fluorescent light intensity.

Figure 1:
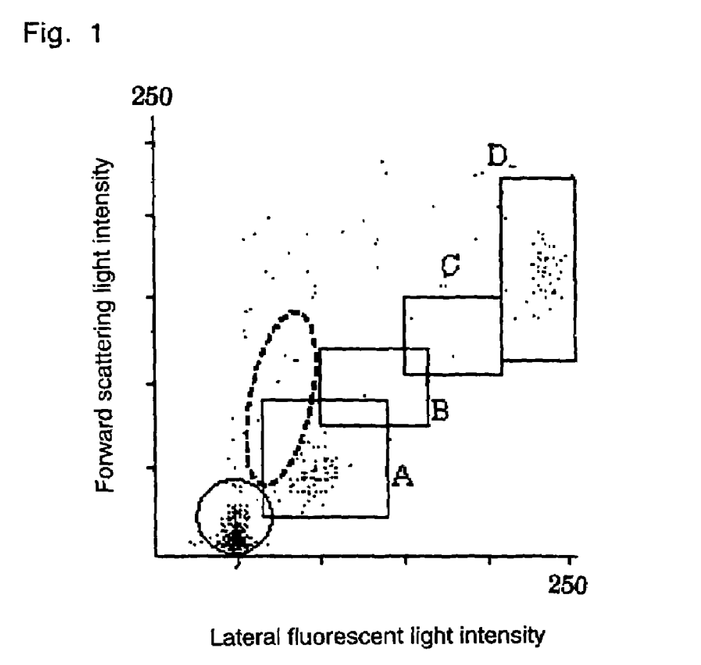
FIG. 1 shows a scattergram of forward scattering light intensity and lateral fluorescent light intensity measured by a method embodying features of the present invention.

The scattergram obtained from the forward scattering light intensity and the lateral fluorescent light intensity is shown in FIG. 1. In FIG. 1, the rectangles A to C indicate the gating of the zones where the malaria parasites (ring form, tropozoite, and schizonte, respectively) appeared, while D indicates the gating of the zone where leukocytes appeared. The dotted-lined oval indicates the zone where reticulocytes appeared, while the solid-lined circle indicates the zone where the debris appeared.

As evident from FIG. 1, there was no plot in the zone where the reticulocytes appeared, indicating almost no appearance of reticulocytes.

COMPARATIVE EXAMPLE 1

Similar to the method described in Example 1 of Japanese Unexamined Patent Publication No. 11-75892, only a single surfactant was used in a single treatment for the measurement of blood from a malaria-infected patient.

Typically, 3 mg of acridine orange, 10 mM of tricine, 1000 mg of LTAC, 120 mM of sodium dihydrogen phosphate, and 1 L of purified water were adjusted to pH 9 with sodium hydroxide to prepare a reagent for measuring malaria parasite. One (1) ml of this reagent and 1 μl of a sample described below were incubated. As the sample, peripheral blood from a falciparum malaria patient having 0.9% infection was employed.

Figure 2:
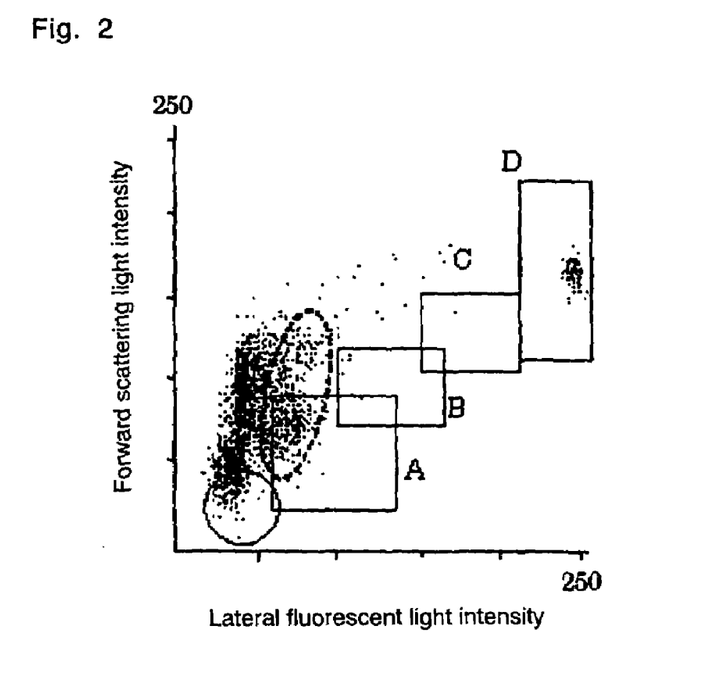
FIG. 2 shows a scattergram of forward scattering light intensity and lateral fluorescent light intensity measured by a conventional method.

The scattergram obtained is shown in FIG. 2. In FIG. 2, the rectangles A to C indicate the zones where the malaria parasites (ring form, tropozoite and schizonte, respectively) appeared, while D indicates the zone where leukocytes appeared. The dotted-lined oval exhibited a large number of reticulocytes which had not undergone sufficient hemolysis.

Thus, there may be false detection of malaria parasites in a specimen even from a non-malaria patient if the reticulocytes which have not undergone sufficient hemolysis appear as being overlapped over the zone where the malaria parasites appear.

In order to intensify the hemolytic activity of the hemolytic agents to dissolve the reticulocytes, thereby reducing the effect of the reticulocytes, the concentration of the surfactant was increased, for example, up to 1000 mg to 10 g as LTAC and the measurement was performed with no change in other compositions.

As a result, it was discovered that increased concentration of surfactant promoted the hemolysis of the reticulocytes but also promoted the dissolution of the malaria parasites. The dissolution of the malaria parasites resulted in a reduction in both the scattering light intensity and the fluorescent light intensity from the malaria parasites, which led to overlapping of the malaria parasites with erythrocyte debris on the scattergram, which made it difficult to obtain a correct measurement.

A similar measurement was conducted using each of three nonionic surfactants employed widely for hemolysis, which have especially high hemolytic activities—namely, polyoxyethylene (40) nonylphenyl ether, polyoxyethylene (100) nonylphenyl ether, and polyoxyethylene (10) lauryl ether—instead of the surfactant described above. No other change in composition from that in Example 1 of Japanese Unexamined Patent Publication No. 11-75892 was made. The osmotic pressure of each surfactant in this measurement ranged from 0.2 to 2.0 mg/L.

As a result, all surfactants affected the measurement at low concentrations by causing an overlapping of the reticulocytes which had not undergone hemolysis with the malaria parasite zones.

A higher concentration enabled the hemolysis of the reticulocytes but also dissolved the parasites, resulting in a reduction in both the scattering light intensity and the fluorescent light intensity, which caused overlapping with erythrocyte debris.

COMPARATIVE EXAMPLE 2

First, a large number of the malaria-infected specimens, the % infections of which had been verified microscopically, were measured by the method of Example 1 above (hereinafter referred to as Method B), and the correlation between the % infection and the number of plots appearing in the ring form zone was obtained. The correlation is shown in FIG. 3.

Figure 3:
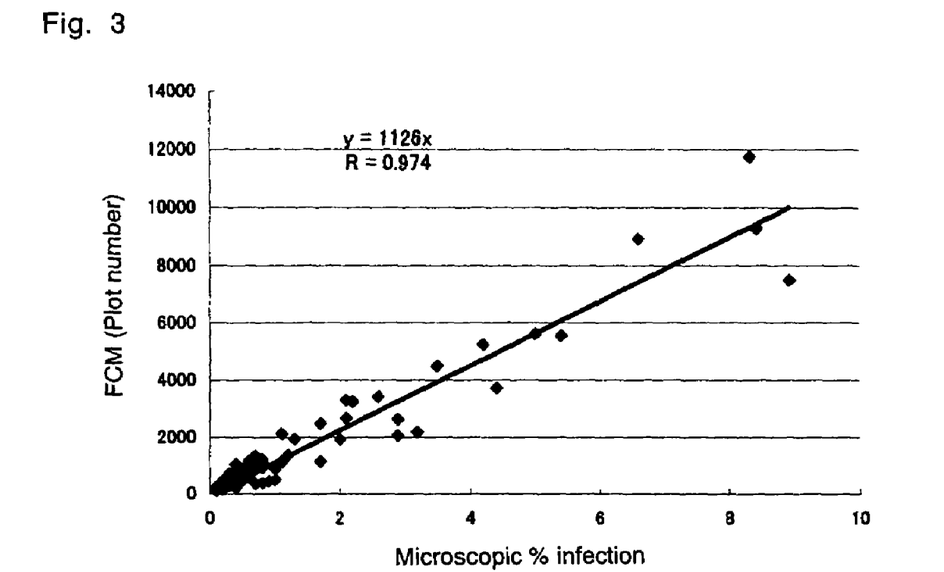
FIG. 3 shows a correlation diagram between percent infection and the number of plots appearing in a ring form zone obtained by the method of Example 1.

Based on the linear regression curve of the correlation shown in FIG. 3, the number of plots corresponding to 0.1% infection was 113.

Next, the specimen of a patient who had been verified to have no malaria was measured by the method described in Example 1 of Japanese Unexamined Patent Publication No. 11-75892 (hereinafter referred to as Method A) and by Method B. The numbers of the plots in the ring form zones on the scattergrams were compared with each other.

When 137 specimens were measured by Method A, the ratio of specimens having a number of plots in the ring form zones of 113 or more was 52.5%. On the other hand, when 542 specimens were measured by Method B, the ratio of specimens having a number of plots in the ring form zones of 113 or more was 4.1%.

Thus, when the detection sensitivity is assumed to correspond to 0.1% infection, Method A appears to give a false indication that 52.5% of the 137 specimens which were actually not infected with malaria were malaria-infected specimens. On the other hand, Method B gave only 4.1% as the ratio of specimens mistakenly judged to be malaria-infected specimens, thus showing a substantially improved measurement accuracy.

COMPARATIVE EXAMPLE 3

Several malaria patients having different % infections were measured by Method A and Method B, and the measurement sensitivity of each method was obtained. In this experiment, the possibility of detection of the malaria parasite was validated as described below.

*Possibility of Detection:

On a scattergram obtained by measuring a specimen, the malaria parasites appear together as a population within a certain zone. The peripheral blood specimen of a malaria-infected patient was measured by the method in Example 1 described above, and a scattergram was obtained. The scattergram is shown in FIG. 4.

Figure 4:
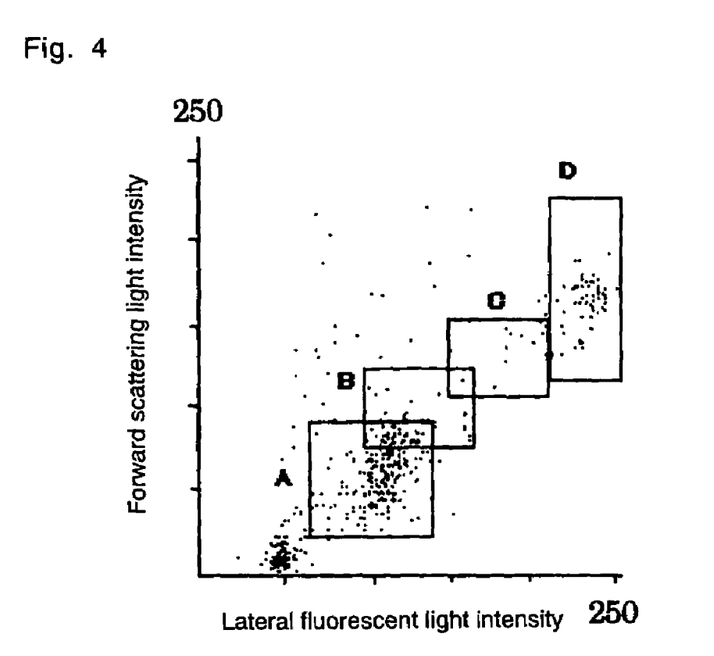
FIG. 4 shows a scattergram obtained by measuring a peripheral blood specimen from a malaria-infected patient by an inventive malaria parasite detection method embodying features of the present invention.

In FIG. 4, the ordinate represents the forward scattering light intensity, while the abscissa represents the lateral fluorescent light intensity. Each detection intensity range of the forward scattering light intensity and the lateral fluorescent light intensity was divided into 255 sections and the coordinates were scaled.

Figure 5:
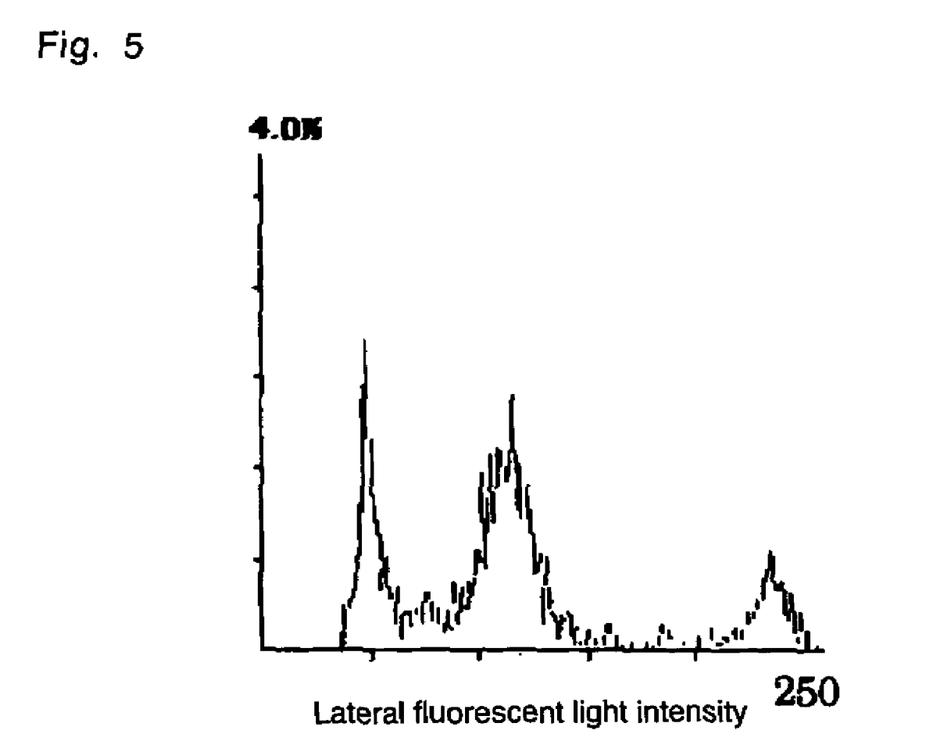
FIG. 5 shows a histogram corresponding to the scattergram of FIG. 4.

When a histogram is produced using fluorescent light intensity as a parameter, the population of the malaria parasites appears in the range of the fluorescent light intensity corresponding to the zone where the malaria parasites appear (coordinates 65 to 210), exhibiting a mount-like shape.

FIG. 5 shows the histogram corresponding to the scattergram in FIG. 4, in which the ordinate represents the frequency (%) and the abscissa represents the fluorescent light intensity.

It was revealed that the population also appeared in the histogram corresponding to the population of the ring form in the scattergram.

As a result of further investigation, the population of the malaria parasite appearing in the histogram was revealed to be within the range from 30 to 80 as the width of this population at the half of the peak height (hereinafter referred to as half-peak width).

However, when the zone where the ring form appears on the scattergram is contaminated with a large number of reticulocytes, then a population of reticulocytes having a large half-peak width appears as overlapping with the position where the ring form population appears. When such a population appears, it is difficult to judge whether only the reticulocytes were involved or both the reticulocytes and the ring form were involved. Accordingly, for a population with a half-peak width exceeding 80, the detection of malaria is regarded as being impossible. The noise appearing in the histogram has short peak heights. In order to distinguish these from the malaria parasite population, only a population with a peak height exceeding 0.4% of the entire frequency was regarded to be malaria parasite population.

Based on the discussion above, when the presence of a population fulfilling both criteria—namely, that the half-peak width is within the range from 30 to 80, and that the height exceeds 0.4% of the entire frequency—is identified in the zone where the malaria parasites are detected (coordinates 65 to 210 with regard to the fluorescent light intensity), then the detection of the malaria is judged to be possible without any effect of the reticulocytes. On the contrary, when a population fulfilling both criteria is not identified in the measurement of a specimen from a malaria patient, then the detection of the malaria is regarded to be impossible.

The results of the investigation of the sensitivity of the malaria parasite detection methods described above is as follows:

Method A
% Infection for measurement possible in all specimens: 0.5% or more
% Infection for measurement impossible in all specimens: less than 0.1%
(the measurement was possible in about 38% of specimens with a % infection of 0.1% or higher and less than 0.5%)

Method B
% Infection for measurement possible in all specimens: 0.1% or more
% Infection for measurement impossible in all specimens: less than 0.05%
(the measurement was possible in about 45% of specimens with a % infections of 0.05% or higher and less than 0.1%)

Accordingly, Method B enabled malaria detection in specimens having a lower % infection than is possible with Method A.

As described above, the present invention enables rapid and specific detection of malaria parasites in samples without requiring complicated operations (e.g., centrifugation).

Especially by adding hemolytic agents to a sample in at least two steps, sufficient hemolysis of erythrocytes and reticulocytes is accomplished while causing no damage to malaria parasites which may affect the measurement, thereby enabling a correct measurement of the malaria parasites in the sample.

The foregoing detailed description and accompanying drawings have been provided by way of explanation and illustration, and are not intended to limit the scope of the appended claims. Many variations in the presently preferred embodiments illustrated herein will be obvious to one of ordinary skill in the art, and remain within the scope of the appended claims and their equivalents.

What is claimed is:

1. A method for detecting a malaria parasite comprising:
    treating a sample treated with an anticoagulant with a first hemolytic agent comprising a first surfactant to form a first treated sample;
    treating the first treated sample with a second hemolytic agent comprising a second surfactant to form a second treated sample, wherein the second surfactant has a hemolytic activity higher than a hemolytic activity of the first surfactant;
    staining the second treated sample with a fluorescent dye to form a stained sample;
    introducing the stained sample into a flow cytometer;
    measuring fluorescent light intensity emitted by the stained sample; and
    distinguishing the malaria parasite based on differences in measured fluorescent light intensities.

2. The method of claim 1, wherein the first surfactant comprises a nonionic surfactant.

3. The method of claim 1, wherein the second surfactant comprises an anionic surfactant.

4. The method of claim 1 wherein the first surfactant and the second surfactant are independently selected from the group consisting of a nonionic surfactant, an anionic surfactant, and a cationic surfactant.

5. The method of claim 4 wherein the nonionic surfactant has a formula:

wherein:
R$_1$ is an alkyl, alkenyl or alkynyl group having 10 to 22 carbon atoms;
R$_2$ is —O—, —(C$_6$H$_4$—O— or —COO—; and
n is an integer from 8 to 120.

6. The method of claim 5 wherein the nonionic surfactant is a polyoxyethylene (n) alkylphenyl ether.

7. The method of claim 5 wherein the nonionic surfactant is selected from the group consisting of polyoxyethytene (40) nonylphenyl ether, polyoxyethylene (100) nonylphenyl ether, and polyoxyathylene (10) lauryl ether.

8. The method of claim 4 wherein the anionic surfactant has a formula:

wherein:
R$_1$ is an alkyl, alkenyl or alkynyl group having 10 to 22 carbon atoms;
R$_2$ is —O—, —(C$_6$H$_4$—O— or —COO—; and
n is an integer from 8 to 120; and
X is SO$_3$Na, COONa, OSO$_3$Na or ONa.

9. The method of claim 4 wherein the cationic surfactant has a formula selected from the group consisting of and
wherein:
R$^a$ is an alkyl, alkenyl or alkynyl group having 8 to 20 carbon atoms;
each of R$^b$, R$^c$ and R$^d$, independently, is an alkyl, alkenyl or alkynyl group having 1 to 8 carbon atoms;
each of X$^-$ and Y$^-$, independently, is an anion; and
m is an integer from 7 to 19.

10. The method of claim 9 wherein the cationic surfactant is selected from the group consisting of octyltrimethylammonium bromide, decyltrimethylammonium bromide, lauryltrimethylammonium chloride, myristyltrimethylammonium bromide, and cetylpyridinium chloride.

11. The method of claim 1 wherein the first surfactant and the second surfactant are independently selected from the group consisting of polyethylene glycol mono[p-(1,1,3,3-tetramethylbutyl)phenyl] ether, 3-[(3-chloroamidopropyl) dimethylammonio] propanesulfonic acid, 3-[(3-chloroamidopropyl)dimethylammonio]-2-hydroxypropanesulfonic acid, N, N-bis(3-D-gluconamidopropyl)deoxychloramide, sucrose monocaprate, sucrose monocholate, n-octyl-α-D-glucopyranoside, n-heptyl-α-D-thioglucopyranoside, n-octyl-α-D-thioglucopyranoside, n-dodecyl-α-D-maltopyranoside, and n-nonyl-α-D-thiomaltopyranoside.

12. The method of claim 1 wherein the fluorescent dye is selected from the group consisting of acridine orange, thiazole orange, ethidlum bromide, propidium iodide, auramine O, Hoechst 33258, Hoechst 33342, rhodamine 123, and DiOC1(3).

13. The method of claim 1 wherein the fluorescent dye has a structure:

wherein:
R$_1$ is a hydrogen atom or a lower alkyl group;
each of R$_2$ and R$_3$, independently, is a hydrogen atom, a lower alkyl group or a lower alkoxy group;
R$_4$ is a hydrogen atom, an acyl group or a lower alkyl group;
R$_5$ is a hydrogen atom or an optionally substituted lower alkyl group;
Z is a sulfur atom, an oxygen atom or a carbon atom substituted by two lower alkyl groups;
n is 1 or 2; and
X$^-$ is an anion.

14. The method of claim 1 wherein the fluorescent dye has a structure:

wherein:
R$_1$ is a hydragen atom or an alkyl group;
each of R$_2$ and R$_3$, independently, is a hydrogen atom, a lower alkyl group or a lower alkoxy group;
R$_4$ is a hydrogen atom, an acyl group or an alkyl group;
Z is a sulfur atom, oxygen atom or carbon atom substituted by two lower alkyl groups;
n is 0, 1 or 2; and
X$^-$ is an anion.

15. The method of claim 1 wherein the fluorescent dye is selected from the group consisting of acridine homodimer, actinomycin D, 7-aminoactinomycin D, 9-amino-6-chloro-2-methoxyacridine, BOBO-1, BOBO-3, BO-PRO-1, BO-PRO-3, 4',6-diamidino-2-phenylindole, dihydroethidium, 4',6-(diimidazolin-2-yl)-2-phenylindole, ethidium-acridine heterodimer, ethidium diazide, ethidium homodimer-1, ethidium homodimer-2, ethidium monoazide, hexidium iodide, hydroxystilbamidine, methanesulfonate, LDS 751, OilGreen ssDNA quantitation reagent PicoGreen dsDNA quantitation reagent, PO-PO-1, PO-PO-3, PO-PRO-1, PO- PRO-3, SYTO 11 live-cell nucleic acid stain, SYTO 12 live-cell nucleic acid stain, SYTO 13 live-cell nucleic acid stain, SYTO 14 live-cell nucleic acid stain, SYTO 15 live-cell nucleic acid stain, SYTO 16 live-cell nucleic acid stain, SYTO 20 live-cell nucleic acid stain, SYTO 21 live-cell nucleic acid stain, SYTO 22 live-cell nucleic acid stain, SYTO 23 live-cell nucleic acid stain, SYTO 24 live-cell nucleic acid stain, SYTO 25 live-cell nucleic acid stain, SYTO 17 red fluorescent nucleic acid stain, SYTOX green nucleic acid stain, TO-PO-1, TO-PRO-3, TO-PRO-5, TO-TO-1, TO-TO-3, YO-PRO-1, YO-PRO-3, YO-YO-1, and YO-YO-3.

16. The method of claim 1 wherein the anticoagulant is selected from the group consisting of EDTA, heparin, citric acid, and citrate.

* * * * *

UNITED STATES PATENT AND TRADEMARK OFFICE
CERTIFICATE OF CORRECTION

| | | |
|---|---|---|
| PATENT NO. | : 7,236,236 B2 | Page 1 of 1 |
| APPLICATION NO. | : 10/678536 | |
| DATED | : June 26, 2007 | |
| INVENTOR(S) | : Nobuaki Hanaoka et al. | |

It is certified that error appears in the above-identified patent and that said Letters Patent is hereby corrected as shown below:

In the Claims

Column 15, in claim 8, line 3 (in the formula), delete "H," and insert --X-- in its place.

Column 15, in claim 8, line 7, after ";" delete "and".

Column 15, in claim 9, in the formula, after "$X^-$" delete "," (comma).

Column 15, in claim 9, insert --and-- between the structures.

Column 16, in claim 14, in the formula, immediately after "$R_4$" delete "," (comma), and delete "$R_8$" and substitute --$R_3$-- in its place.

Column 16, in claim 14, in the 2$^{nd}$ line following the formula, delete "hydragen" and substitute --hydrogen-- in its place.

Signed and Sealed this

Twentieth Day of November, 2007

JON W. DUDAS
*Director of the United States Patent and Trademark Office*